(12) United States Patent
Ohashi

(10) Patent No.: US 6,740,153 B2
(45) Date of Patent: May 25, 2004

(54) BIPYRROLINONYLIDENE-TYPE COMPOUND, COLORANT THEREWITH, AND METHOD OF PRODUCTION THEREOF

(75) Inventor: Yuji Ohashi, Sakura (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 10/384,707

(22) Filed: Mar. 11, 2003

(65) Prior Publication Data

US 2003/0172478 A1 Sep. 18, 2003

(30) Foreign Application Priority Data

Mar. 13, 2002 (JP) ........................ 2002-068389

(51) Int. Cl.[7] ........................ C09B 7/00; C07D 207/02
(52) U.S. Cl. ...................... 106/31.78; 548/518
(58) Field of Search ................... 106/31.78; 548/518

(56) References Cited

PUBLICATIONS

Morton, et al, Jul. 2002, Tetrahedron, 58, 5547–5565.*
von Alfred Treibs, et al.; Liebigs Ann. Chem. 702, pp. 112–130, 1967.
Loukaci, Ali et al: "Trikendiol, an unusual red pigment from the sponge Trikentrion loeve, anti–HIV–1 metabolite" Tetrahedron Letters (1994) 35(37), 6869–72.
Treibs, Alfred et al: "Isoindigo dyes of the pyrrole series" Justus Liebigs Ann. Chem. (1967), 702, 112–30.
Fiesselmann, Hans et al: "Methylenedeoxybenzoins. VIII. The reaction of gamma.–oxo acids with ammonium acetate" Chemische Berichte (1958), 91, 1713–19.
Knott, Edward B.: ".beta.Cycloylpropionitriles, II. Conversion into bis–2–(5–cyclypyrrole)azamethin salts" Journal of the Chemical Society, Abstracts (1947) 1196–1201.

* cited by examiner

Primary Examiner—Joseph K. McKane
Assistant Examiner—Andrea D. Small
(74) Attorney, Agent, or Firm—Armstrong, Kratz, Quintos, Hanson & Brooks, LLP

(57) ABSTRACT

A bipyrrolinonylidene-type compound is provided which is useful as colorants such as dyes and pigments, or other organic chemical products or intermediates thereof. A method of producing the bipyrrolinonylidene-type compound is also provided, which is suitable for large-scale industrial production with high yield. The bipyrrolinonylidene-type compound is represented by general formula (1).

General Formula (1)

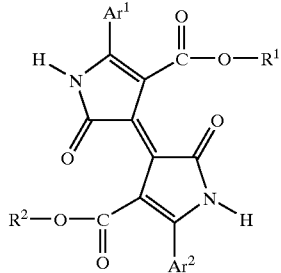

The bipyrrolinonylidene-type compound is obtained by oxidizing a pyrrolinone-type compound represented by the general formula (3) in the presence of an anthraquinone-type catalyst.

General Formula (3)

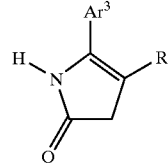

13 Claims, No Drawings

BIPYRROLINONYLIDENE-TYPE COMPOUND, COLORANT THEREWITH, AND METHOD OF PRODUCTION THEREOF

BACKGROUND OF THE INVENTION

1. Field of the Invention

The present invention relates to bipyrrolinonylidene-type compounds which are useful as colorants such as dyes and pigments, and relates to methods of producing the same.

2. Description of Related Art

A method of producing bipyrrolinonylidene represented by the formula (b):

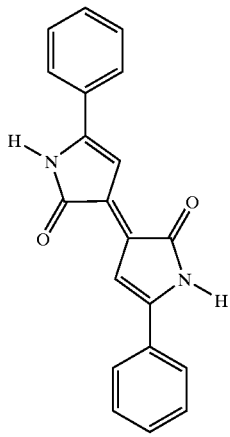

by air-oxidizing pyrrolinone represented by the formula (a):

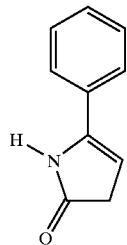

is disclosed (see Liebigs Ann. Chem., 702, 112–130 (1967)).

However, the yield in the above method is low, such as 10 to 15%, and the method is not suitable for large-scale industrial production of bipyrrolinonylidene.

Also, it was difficult to employ bipyrrolinonylidene represented by the formula (b) as dyes and pigments, or other organic chemical products or intermediates thereof because of its poor solubility in water and organic solvents.

BRIEF SUMMARY OF THE INVENTION

An object of the present invention is to provide bipyrrolinonylidene-type compounds which are useful as colorants such as dyes and pigments, or other organic chemical products or intermediates thereof, and also provides a method of producing the bipyrrolinonylidene-type compound, which is suitable for large-scale industrial production with high yield.

The present inventors have found that a bipyrrolinonylidene-type compound, which develops a vivid navy blue color and is soluble in various organic solvents, can be produced with high yield by air-oxidizing a pyrrolinone compound using a specific catalyst, and thus the present invention has been completed.

To achieve the above object, the present invention provides a bipyrrolinonylidene-type compound represented by the general formula (1):

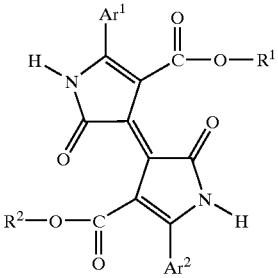

wherein $Ar^1$ and $Ar^2$ each independently represents an aryl group, and $R^1$ and $R^2$ each independently represents a hydrogen atom, an alkyl group having 1 to 18 carbon atoms, a cycloalkyl group having 3 to 18 carbon atoms, or an aryl group.

To achieve the above object, the present invention also provides a method of producing a bipyrrolinonylidene-type compound represented by the general formula (4):

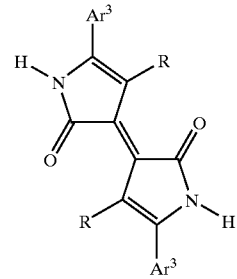

wherein $Ar^3$ represents an aryl group, and R represents a hydrogen atom, a halogen atom, a cyano group, a hydroxyl group, an alkyl group, an alkoxyl group, an amino group, an alkylamino group, a cycloalkyl group, a cycloalkyloxy group, an aryl group, an alkoxycarbonyl group, a cycloalkyloxycarbonyl group, a carbamoyl group, a nitro group, a carboxyl group or a sulfonic acid group, which comprises oxidizing a pyrrolinone-type compound represented by the general formula (3):

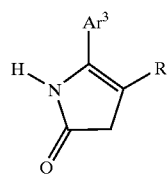

wherein $Ar^3$ represents an aryl group, and R represents a hydrogen atom, a halogen atom, a cyano group, a hydroxyl group, an alkyl group, an alkoxyl group, an amino group, an alkylamino group, a cycloalkyl group, a cycloalkyloxy group, an aryl group, an alkoxycarbonyl group, a cycloalkyloxycarbonyl group, a carbamoyl group, a nitro group, a carboxyl group or a sulfonic acid group in the presence of an anthraquinone-type catalyst.

The bipyrrolinonylidenedicarboxylic acid-type compound represented by the general formula (1) of the present invention can be used as a dye, as it is, because it develops a vivid navy blue color, or a metal salt of bipyrrolinonylidenedicarboxylic acid can be used as a pigment.

According to the method of the present invention, the bipyrrolinonylidene-type compound represented by the general formula (4) can be produced by a simple method of air-oxidizing a pyrrolinone compound in the presence of an anthraquinone-type catalyst. The bipyrrolinonylidene-type compound represented by the general formula (4) obtained by the method of the present invention is soluble in various solvents as compared with conventionally known bipyrrolinonylidene and is also useful as dyes and pigments, or other organic chemical products or intermediates thereof because it has a carboxyl group or an ester bond.

DETAILED DESCRIPTION OF THE INVENTION

The present invention will now be described.

In the bipyrrolinonylidene-type compound represented by the general formula (1) used in the present invention, $Ar^1$ and $Ar^2$ each independently represents an aryl group. Examples of the aryl group include aromatic ring groups such as a phenyl group, naphthalene group, anthracene group, phenanthrene group, pyrene group or biphenyl group; and aromatic hetero ring groups such as a pyrrole group, pyrazole group, imidazole group, pyridine group, pyrimidine group, pyrazine group, indole group, quinoline group, carbazole group, furan group or thiazole group.

Also these aromatic rings may have substituents. Examples of the substituents include a hydrogen atom, halogen atom, cyano group, hydroxyl group, alkyl group, amino group, alkylamino group, alkoxyl group, aryl group, alkoxycarbonyl group, carbamoyl group, nitro group, sulfonic acid group and sulfonate group. Among these substituents, a halogen atom or sulfonic acid group is preferred. When the substituent is a halogen, the bipyrrolinonylidenedicarboxylic acid derivative (A) tends to exhibit higher chemical stability. When the substituent is a sulfonic acid group or a sulfonic acid metal salt group, the bipyrrolinonylidenedicarboxylic acid derivative (A) tends to exhibit higher solubility in water or organic solvents.

When the aromatic ring is substituted with plural halogen atoms, halogen atoms may be the same or different. When the halogen atom is a chlorine atom or a bromine atom, the bipyrrolinonylidenedicarboxylic acid derivative (A) tends to exhibit higher chemical stability and, therefore, it is preferred.

In the general formula (1), $R^1$ and $R^2$ each independently represents a hydrogen atom, an alkyl group having 1 to 18 carbon atoms, a cycloalkyl group having 3 to 18 carbon atoms, or an aryl group. It is preferred that $R^1$ and $R^2$ each independently represents a hydrogen atom or an alkyl group having 1 to 18 carbon atoms. Examples of the alkyl group having 1 to 18 carbon atoms include alkyl groups such as a methyl group, ethyl group, n-propyl group, isopropyl group, n-butyl group, isobutyl group or n-octadecyl group; and cycloalkyl groups such as a cyclohexyl group. It is preferred that the bipyrrolinonylidene-type compound represented by the general formula (1) tends to exhibit higher heat stability when $R^1$ and $R^2$ each independently represents an alkyl group having 1 to 8 carbon atoms.

Among the bipyrrolinonylidene-type compounds represented by the general formula (1), a bipyrrolinonylidene-type compound represented by the general formula (2):

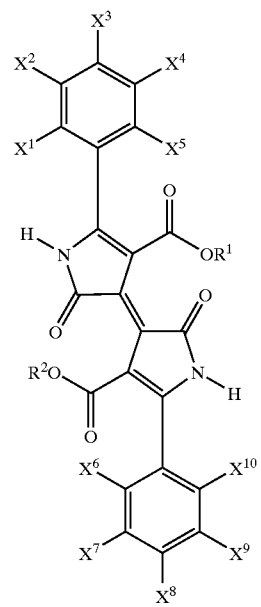

wherein $X^1$, $X^2$, $X^3$, $X^4$, $X^6$, $X^7$, $X^8$, $X^9$ and $X^{10}$ each independently represents a hydrogen atom, a halogen atom, a cyano group, a hydroxyl group, an alkyl group, an amino group, an alkylamino group, an alkoxyl group, an aryl group, an alkoxycarbonyl group, a cycloalkyloxycarbonyl group, a carbamoyl group, a nitro group, a sulfonic acid group or a sulfonate group, and $R^1$ and $R^2$ each independently represents a hydrogen atom, an alkyl group having 1 to 18 carbon atoms, a cycloalkyl group having 3 to 18 carbon atoms, or an aryl group is preferred.

The bipyrrolinonylidene-type compound represented by the general formula (1) used in the present invention has high solubility in water or organic solvents because it has a carboxyl group or an ester bond in a molecule, and also the bipyrrolinonylidene-type compound can be used as a dye, as it is, because it develops a blue to violet color hue. Among the compounds represented by the general formula (1), a metal salt of a bipyrrolinonylidene-type compound in which $R^1$ and $R^2$ are hydrogen atoms can be used as a pigment because it is insoluble in water or organic solvents.

Among the bipyrrolinonylidene-type compounds used in the present invention, a bipyrrolinonylidene-type compound in which $R^1$ and $R^2$ are hydrogen atoms has the solubility in water and an organic solvent, and solubility suitable for the objective purposes can be imparted by reacting with a carboxyl group thereby introducing various atomic groups.

Among the bipyrrolinonylidene-type compounds represented by the general formula (1) used in the present invention, a metal salt or ester of the compound in which $R^1$ and $R^2$ are hydrogen atoms will now be described.

With respect to the bipyrrolinonylidene-type compound represented by the general formula (1) used in the present invention, either or both of two carboxyl groups may form a salt with a metal atom, while the solubility of the metal salt formed is drastically influenced by the kind of the metal atom. When the metal atom is an alkali metal such as sodium or potassium, the metal salt is soluble in water. When the metal salt is a polyvalent metal such as calcium, barium, aluminum or strontium, the metal salt is insoluble in water. When using the colorant of the present invention as a pigment for printing ink, the colorant is preferably insoluble in water and a polyvalent metal salt such as calcium or aluminum is preferably used.

With respect to the bipyrrolinonylidene-type compound represented by the general formula (1) used in the present invention, either or both of two carboxyl groups may form an ester. Examples of the ester include esters with an aliphatic monohydric alcohol, such as a methyl ester, ethyl ester, n-propyl ester, n-butyl ester, i-butyl ester, n-hexyl ester, n-octyl ester, n-decyl ester or n-octadecyl ester; esters with aliphatic polyhydric alcohols, such as a 2-hydroxyethyl ester, 2,3-dihydroxypropyl ester, 4-hydroxybutyl ester or 6-hydroxyhexyl ester; and esters with unsaturated alcohols, such as a benzyl ester, allyl ester, 2-(methacryloyl)-ethyl ester or 2-(tetrahydropyranyloxy)-ethyl ester. Among these, an ester with an aliphatic alcohol is preferred in view of high chemical stability of the ester group.

The bipyrrolinonylidene-type compound used in the present invention has a vivid color hue in a color ranging from blue to violet because of the chemical structure of the aryl groups $Ar^1$ and $Ar^2$, the kind of a metal atom which forms a salt, or the chemical structure of an ester and, therefore, it can be widely used, as a colorant, in fiber colorants, printing inks, color filters, automotive coating compositions, and plastic colorants. The bipyrrolinonylidenedicarboxylic acid derivative (A) in the present invention itself has a sufficient tinting power, but toning can be conducted by mixing with other colorants.

The bipyrrolinonylidene-type compound used in the present invention is obtained by oxidizing the pyrrolinone-type compound represented by the general formula (3). In the present invention, the bipyrrolinonylidene-type compound represented by the general formula (4) can be produced by oxidizing the pyrrolinone-type compound represented by the general formula (3) in the presence of an anthraquinone-type catalyst.

By the method of producing a bipyrrolinonylidene-type compound of the present invention, the bipyrrolinonylidene-type compound represented by the general formula (1) can be produced using, as a starting material, the pyrrolinone-type compound of the general formula (3) in which R is a carboxyl group or an alkoxycarbonyl group having 1 to 18 carbon atoms.

In the general formula (3) and the general formula (4), examples of the aryl group represented by $Ar^3$ include groups having an aromatic ring, such as benzene, naphthalene, anthracene, phenanthrene, pyrene or biphenyl; and groups having an aromatic hetero ring, such as pyrrole, pyrazole, imidazole, pyridine, pyrimidine, pyrazine, indole, quinoline, carbazole, furan or thiazole. The fewer the aromatic rings or aromatic hetero rings in the aryl group, the higher the solubility of the resulting bipyrrolinonylidene-type compound in an organic solvent. The aryl group may have a substituent. Examples of the substituent include a halogen atom, cyano group, hydroxyl group, alkyl group, amino group, alkylamino group, alkoxyl group, aryl group, alkoxycarbonyl group, cycloalkyloxycarbonyl group, carbamoyl group, nitro group, sulfonic acid group and sulfonate group. When the substituent is a halogen atom, the resulting compound tends to exhibit higher chemical stability. When the substituent is a sulfonic acid group which may form a salt with a metal atom, the resulting bipyrrolinonylidene-type compound tends to exhibit higher solubility in water or organic solvents.

In the general formula (3) and the general formula (4), R represents a halogen atom, a cyano group, a hydroxy group, an amino group which may be substituted with an alkyl group, an alkoxy group, a cycloalkyloxy group, an alkyl group, a cycloalkyl group, an aryl group, an alkoxycarbonyl group, a cycloalkyloxycarbonyl group, a carbamoyl group, a nitro group, a carboxyl group which may form a salt with a metal atom, or a sulfonic acid group which may form a salt with a metal atom. When the substituent is a cyano group, an alkyl group, an aryl group, an alkoxycarbonyl group, or a carboxyl group which may form a salt with a metal atom, the resulting bipyrrolinonylidene-type compound tends to exhibit higher chemical stability.

In the method of producing the bipyrrolinonylidene-type compound of the present invention, examples of the anthraquinone-type catalyst include sodium anthraquinone-β-sulfonate and sodium anthraquinone-β,β'-disulfonate. The amount of the anthraquinone-type catalyst is preferably used in an amount within a range from 1 to 50 mol %, and more preferably from 2 to 30 mol %, based on the pyrrolinone-type compound represented by the general formula (3).

In the oxidizing reaction of the pyrrolinone-type compound represented by the general formula (3), a solvent is preferably used. Examples of usable solvents include solvents which are less likely to be oxidized in the presence of the anthraquinone-type catalyst, for example, aromatic solvents such as nitrobenzene, toluene and xylene; alcohols such as methanol, ethanol, isopropanol, isobutanol and ethylene glycol monobutyl ether; esters such as ethyl acetate, butyl acetate and 2-etoxyethyl acetate; aprotic polar solvents such as N-methylpyrrolidone; and water and a mixed solvent of water and a water-soluble organic solvent. Among these solvents, nitrobenzene having a high ability of dissolving the pyrrolinone-type compound represented by the general formula (3), or a mixed solvent of nitrobenzene and the other organic solvent is preferred because high yield is achieved.

In the present invention, various oxidizing agents can be used. Specific examples thereof include peroxides such as hydrogen peroxide, m-chloroperbenzoic acid, peracetic acid, perchloric acid or potassium permanganate, or oxygen or air. When using air, there can he obtained such an advantage that high safety is achieved and manufacturing cost can be reduced. In the oxidizing reaction using air as an oxidizing agent, an inert gas such as nitrogen may be mixed with the air for the purpose of raising a lower limit of the explosive limit concentration of the reaction system.

In the oxidizing reaction, the reaction system may be heated for the purpose of increasing the reaction rate and the reaction system is preferably stirred for the purpose of allowing the oxidizing reaction to proceed uniformly. In the case of the oxidizing reaction using air as an oxidizing agent, the reaction temperature is controlled within a range from 100 to 250° C., preferably from 140 to 230° C., and more preferably from 170 to 210° C., and air is preferably supplied uniformly into the reaction system after stirring sufficiently.

The bipyrrolinonylidene-type compound represented by the general formula (1) used in the present invention can be produced by the method of producing the bipyrrolinonylidene-type compound represented by the general formula (4) using the pyrrolinonylidene-type compound represented by the general formula (3).

EXAMPLES

The present invention will now be described in detail by way of Examples. In the following Examples, parts and percentages are by weight unless otherwise specified.

Example 1

A mixture of 7.5 parts of ethyl phenylpyrrolinonecarboxylate represented by the formula (5):

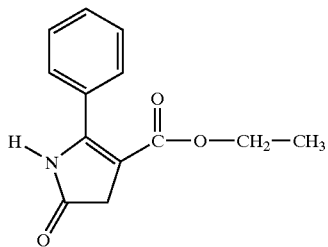

0.75 parts of sodium anthraquinone-β-sulfonate and 275 parts of nitrobenzene was heated to 180° C. with stirring in an air flow. After stirring at the same temperature for one hour, the mixture was air-cooled to room temperature with stirring. Nitrobenzene was distilled off from the strong Prussian blue reaction mixture under reduced pressure and 230 parts of hexane was added to the blackish navy blue solid remaining in the reaction vessel, followed by refluxing with stirring for one hour, suction filtration and further washing with hexane. The resulting product was recrystallized from ethyl acetate to obtain 6.0 parts of a strong navy blue crystal (yield: 80%) having a melting point of 330° C. and a visible light maximum absorption wavelength (λmax) of a dimethyl sulfoxide solution of 574 nm. The resulting strong navy blue crystal was subjected to IR (infrared spectroscopic) analysis, NMR (nuclear magnetic resonance spectrum) analysis and EI-MS (electron impact-mass spectrum) analysis to obtain the following results.

IR Analysis Results 3170 cm$^{-1}$: N—H stretching vibration of pyrrolinone ring amide —CONH—

2990 cm$^{-1}$: C—H stretching vibration of ethyl ester —COOCH$_2$CH$_3$ 1725 cm$^{-1}$: C=O stretching vibration of ethyl ester —COOCH$_2$CH$_3$ 1675 cm$^{-1}$: C=O stretching vibration of pyrrolinone ring amide —CONH—

1245 cm$^{-1}$: CO—OCH$_2$CH$_3$ stretching vibration of ethyl ester —COOCH$_2$CH$_3$ 1105 cm$^{-1}$: COO—C stretching vibration of ethyl ester —COOCH$_2$CH$_3$ NMR Analysis Results $^1$H-NMR (d6-DMSO)

11.3 ppm: 2H, s, hydrogen of pyrrolinone ring amide —CONH—

8.1–7.5 ppm: 10H, m, hydrogen of phenyl group 4.1 ppm: 4H, q, methylene hydrogen of ethyl ester —COOCH$_2$CH$_3$ 1.2 ppm: 6H, t, methyl hydrogen of ethyl ester —COOCH$_2$CH$_3$ $^{13}$C-NMR (d6-DMSO)

168 ppm: carbon of pyrrolinone ring amide —CONH—

164 ppm: carbonyl carbon of ethyl ester —COOCH$_2$CH$_3$ 152 ppm: carbon at the 5-position of pyrrolinone ring (carbon adjacent to phenyl group, C$_6$H$_5$—C)

131–128 ppm: carbon of phenyl group 109 ppm: carbon at the 4-position of pyrrolinone ring (carbon adjacent to ester bond, C—COOC$_2$H$_5$)

60 ppm: methylene carbon of ethyl ester —COO—CH$_2$—

14 ppm: methyl carbon of ethyl ester —COOCH$_2$—CH$_3$

EI-MS Analysis Results

As a result of mass spectrometry, a molecular ion peak (M+) of diethyl bipyrrolinonylidenedicarboxylate (molecular weight: 458) was detected at a DI temperature of 110 to 195° C.

The above results revealed that this compound is diethyl bipyrrolinonylidenedicarboxylate having a chemical structure represented by the formula (6):

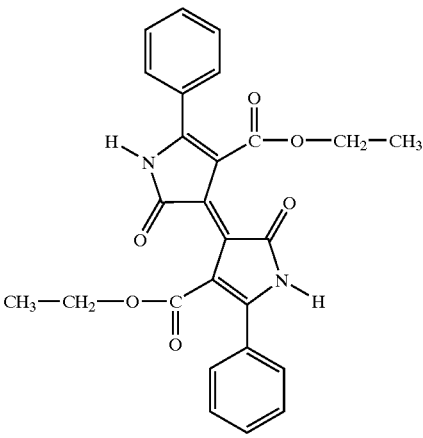

The resulting diethyl bipyrrolinonylidenedicarboxylate was soluble in dimethylformamide and dimethyl sulfoxide and was slightly soluble in ethanol.

Example 2

A mixture of 7.5 parts of ethyl phenylpyrrolinonecarboxylate represented by the formula (5), 0.75 parts of sodium anthraquinone-1,5-disulfonate, 275 parts of nitrobenzene and 20 parts of xylene was heated to 190° C. with stirring in an air flow. Water produced during the reaction was removed out of the reaction system using a Dean-Stark trap. After stirring at the same temperature for one hour, the mixture was air-cooled to room temperature with stirring and the reaction mixture containing the blackish navy blue precipitate was added to 1000 parts of hexane. After stirring at room temperature for 30 minutes, the precipitate was collected by filtration. The precipitate was sequentially washed with hexane and ethyl acetate to obtain a navy blue reaction product, which was dispersed in 1500 parts by water and then stirred at room temperature for 2 hours. After filtration and washing with water, the reaction product was dispersed in 1700 parts of water and stirred at room temperature for one hour. After filtration and washing with water, the reaction product was sufficiently washed with hot water and then dried to obtain 5.6 parts of a navy blue solid (yield: 75%). The resulting strong navy blue crystal was subjected to infrared spectroscopic analysis, NMR analysis and EI-MS analysis and the results revealed that the strong navy blue crystal has the same chemical structure as that of the diethyl bipyrrolinonylidenedicarboxylate represented by the formula (6) obtained in Example 1. The resulting strong navy blue crystal was also subjected to elemental analysis and found to have good accordance with theoretical amounts as shown below.

Elemental Analysis Results

Found: C, 68.05; H, 4.82; N, 6.03%.

Calcd. for C26H22N2O6: C, 68.11; H, 4.84; N, 6.11%.

Example 3

4.6 Parts of diethyl bipyrrolinonylidenedicarboxylate having a chemical structure represented by the formula (6) obtained in Example 2 was added to 350 parts of an aqueous 14% sodium hydroxide solution, and then hydrolyzed with stirring at 50° C. for one hour. After ice-cooling the resulting reddish brown solution, the blackish violet precipitate collected by filtration was dissolved in 1 L of water. The solution was neutralized by adding about 13 parts of 35% hydrochloric acid while stirring with ice-cooling, and then the pH of the solution was adjusted to 1 by adding hydrochloric acid. The brackish brown precipitate obtained by the addition of an acid was subjected to suction filtration, washed with water, washed with acetone and then dried to obtain 0.8 parts of a vivid Prussian blue crystal (yield: 20%) having a visible light maximum absorption wavelength (λmax) of a dimethyl sulfoxide solution of 567 nm. The resulting strong navy blue crystal was subjected to IR (infrared spectroscopic) analysis, NMR (nuclear magnetic resonance spectrum) analysis and EI-MS (electron impact-mass spectrum) analysis to obtain the following results.

IR Analysis Results 3420 cm$^{-1}$: N—H stretching vibration of pyrrolinone ring amide —CONH—

3150 cm$^{-1}$: O—H stretching vibration of carboxyl group —COOH 3060 cm$^{-1}$: C—H stretching vibration of phenyl group —C$_6$H$_5$ 1765 cm$^{-1}$: C=O stretching vibration of carboxyl group —COOH 1680 cm$^{-1}$: C=O stretching vibration of pyrrolinone ring amide —CONH—

1255 cm$^{-1}$: CO—OH stretching vibration of carboxyl group —COOH

NMR Analysis Results $^1$H-NMR(d6-DMSO)

13.5 ppm: 2H, s, hydrogen of carboxyl group —COOH 10.8 ppm: 2H, s, hydrogen of pyrrolinone ring amide —CONH—

8.3–6.9 ppm: 10H, m, hydrogen of phenyl group

The above results revealed that this compound has a chemical structure of bipyrrolinonylidenedicarboxylic acid represented by the formula (7):

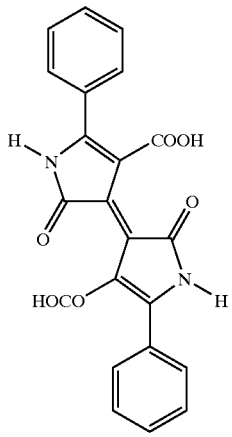

Example 4

0.8 Parts of bipyrrolinonylidenedicarboxylic acid having a chemical structure represented by the formula (7) obtained in Example 3 was added to 100 parts of an aqueous 20% sodium hydroxide solution, and then 95 parts of methanol was further added. After adjusting the pH to 9 by adding hydrochloric acid to the resulting red solution, 4 parts of aluminum sulfate 14–18 hydrate was added. The precipitated blackish navy blue precipitate was subjected to suction filtration, washed with water, washed with acetone and then dried to obtain a strong Prussian blue solid.

The Prussian blue solid obtained in Example 4 was insoluble in hexane, toluene, isopropanol and water, and developed a vivid and strong bluish violet color, and also suitable for use as a pigment for printing ink.

The resulting Prussian blue solid was subjected to IR (infrared spectroscopic) analysis and thermal analysis and the residue obtained by the thermal analysis was subjected to X-ray fluorescence analysis and X-ray powder diffraction analysis revealed the following results.

IR Analysis Results 3430 cm$^{-1}$: N—H stretching vibration of pyrrolinone ring amide —CONH—

1680 cm$^{-1}$: C=O stretching vibration of pyrrolinone ring amide —CONH—

1055 cm$^{-1}$: CO—OAl stretching vibration of carboxylate group —COOAl

Thermal Analysis Results

Organic component: 95.4%, Inorganic component: 4.6%

X-ray Fluorescence Analysis Results

X-ray intensities of mainly detected elements and their proportions (%)

Al 4.15 (47%), Na 0.35 (22%), Si 0.53 (12%), Ca 0.67 (6%)

As is apparent from the results of X-ray fluorescence analysis, Al salt and Na salt exist at a ratio of 47%:22%=1.74 mol %:0.96 mol %≈2 mol:1 mol.

X-Ray Powder Diffraction Analysis Results

Diffraction peaks were observed at θ/2θ=21°, 30°, 33°, and 35°.

All of these peaks correspond to main diffraction peaks of NaAlO$_2$

As is apparent from the above results, the Prussian blue solid of Example 4 has a sodium salt structure, in addition to an Al salt structure.

On the assumption that a ratio of Al to Na determined based on the X-ray fluorescence analysis results of the Prussian blue solid obtained in Example 4 is 2:1, a ratio of a divalent anion [molecular formula =(C$_{22}$H$_{12}$O$_6$N$_2$)$^{2-}$] of bipyrrolinonylidenedicarboxylic acid to Al and Na corresponds to the thermal analysis results was examined. As a result, it has been found that seven (C$_{22}$H$_{12}$O$_6$N$_2$)$^{2-}$, four Al ions and two Na ions exist in a molecule of the Prussian blue solid. Consequently, the Prussian blue solid obtained in example 4 was a lake pigment represented by the composition formula: [(C$_{22}$H$_{12}$O$_6$N$_2$)$^{2-}$]$_7$(Al$^{3+}$)$_4$(Na$^+$)$_2$.

What is claimed is:

1. A bipyrrolinonylidene-type compound represented by the general formula (1):

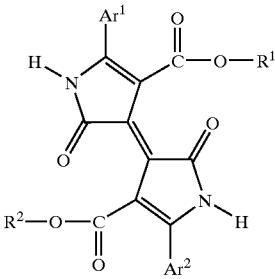

wherein Ar$^1$ and Ar$^2$ each independently represents an aryl group, and R$^1$ and R$^2$ each independently represents a hydrogen atom, an alkyl group having 1 to 18 carbon atoms, a cycloalkyl group having 3 to 18 carbon atoms, or an aryl group.

2. The bipyrrolinonylidene-type compound according to claim 1, which is represented by the general formula (2):

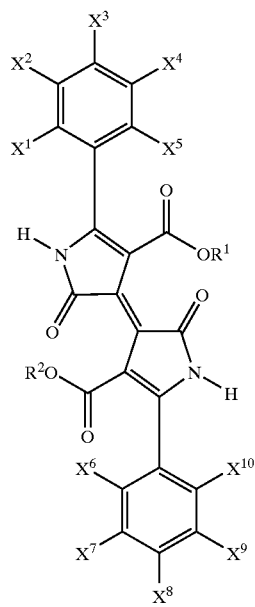

wherein $X^1$, $X^2$, $X^3$, $X^4$, $X^5$, $X^6$, $X^7$, $X^8$, $X^9$ and $X^{10}$ each independently represents a hydrogen atom, a halogen atom, a cyano group, a hydroxyl group, an alkyl group, an amino group, an alkylamino group, an alkoxyl group, an aryl group, an alkoxycarbonyl group, a cycloalkyloxycarbonyl group, a carbamoyl group, a nitro group, a sulfonic acid group or a sulfonate group, and $R^1$ and $R^2$ each independently represents a hydrogen atom, an alkyl group having 1 to 18 carbon atoms, a cycloalkyl group having 3 to 18 carbon atoms, or an aryl group.

3. The bipyrrolinonylidene-type compound according to claim 2, wherein $X^1$, $X^2$, $X^3$, $X^4$, $X^5$, $X^6$, $X^7$, $X^8$, $X^9$ and $X^{10}$ each independently represents a hydrogen atom or a halogen atom, and $R^1$ and $R^2$ each independently represents a hydrogen atom or an alkyl group having 1 to 18 carbon atoms in the general formula (2).

4. The bipyrrolinonylidene-type compound according to claim 2, wherein all of $X^1$, $X^2$, $X^3$, $X^4$, $X^5$, $X^6$, $X^7$, $X^8$, $X^9$ and $X^{10}$ are hydrogen atoms, and $R^1$ and $R^2$ each independently represents a hydrogen atom or an alkyl group having 1 to 8 carbon atoms in the general formula (2).

5. A colorant comprising a bipyrrolinonylidene-type compound or a metal salt of a bipyrrolinonylidene-type compound represented by general formula (1) of claim 1 in which $R^1$ and $R^2$ each represents a hydrogen atom.

6. A colorant comprising a bipyrrolinonylidene-type compound or a metal salt of a bipyrrolinonylidene-type compound represented by general formula (2) of claim 2 in which $R^1$ and $R^2$ each represents a hydrogen atom.

7. The colorant according to claim 6, wherein $X^1$, $X^2$, $X^3$, $X^4$, $X^5$, $X^6$, $X^7$, $X^8$, $X^9$ and $X^{10}$ each independently represents a hydrogen atom or halogen atom, and $R^1$ and $R^2$ each independently represents a hydrogen atom or an alkyl group having 1 to 18 carbon atoms.

8. The colorant according to claim 6, wherein all of $X^1$, $X^2$, $X^3$, $X^4$, $X^5$, $X^6$, $X^7$, $X^8$, $X^9$ and $X^{10}$ are hydrogen atoms, and $R^1$ and $R^2$ each independently represents a hydrogen atom or an alkyl group having 1 to 8 carbon atoms.

9. The colorant according to any one of claims 5 to 8, wherein the metal salt of the bipyrrolinonylidene-type compound is an alkali metal salt.

10. The colorant according to any one of claims 5 to 8, wherein the metal salt of the bipyrrolinonylidene-type compound is a sodium salt or a potassium salt.

11. The colorant according to any one of claims 5 to 8, wherein the metal salt of the bipyrrolinonylidene-type compound is a polyvalent metal salt.

12. The colorant according to any one of claims 5 to 8, wherein the metal salt of the bipyrrolinonylidene-type compound is a calcium salt, a barium salt or an aluminum salt.

13. A method of producing a bipyrrolinonylidene-type compound represented by the general formula (4):

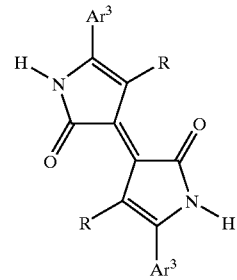

wherein $Ar^3$ represents an aryl group, and R represents a hydrogen atom, a halogen atom, a cyano group, a hydroxyl group, an alkyl group, an alkoxyl group, an amino group, an alkylamino group, a cycloalkyl group, a cycloalkyloxy group, an aryl group, an alkoxycarbonyl group, a cycloalkyloxycarbonyl group, a carbamoyl group, a nitro group, a carboxyl group or a sulfonic acid group, which comprises oxidizing a pyrrolinone-type compound represented by the general formula (3):

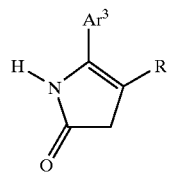

wherein $Ar^3$ represents an aryl group, and R represents a hydrogen atom, a halogen atom, a cyano group, a hydroxyl group, an alkyl group, an alkoxyl group, an amino group, an alkylamino group, a cycloalkyl group, a cycloalkyloxy group, an aryl group, an alkoxycarbonyl group, a cycloalkyloxycarbonyl group, a carbamoyl group, a nitro group, a carboxyl group or a sulfonic acid group in the presence of an anthraquinone-type catalyst.

* * * * *